(12) United States Patent
Schober et al.

(10) Patent No.: US 8,587,647 B2
(45) Date of Patent: Nov. 19, 2013

(54) IMAGER HEAD ADJUSTABLE MIRROR MOUNT FOR BORESCOPE

(75) Inventors: Jeffrey C. Schober, Sterling Heights, MI (US); Shepherd H. Whitcomb, Ann Arbor, MI (US); Owen W. Draper, West Bloomfield, MI (US); Josh T. Guerra, Beverly Hills, MI (US); Tye L. Newman, Howell, MI (US); Al Boehnlein, Ypsilanti, MI (US)

(73) Assignee: Inspectron, Inc., Novi, MI (US)

( * ) Notice: Subject to any disclaimer, the term of this patent is extended or adjusted under 35 U.S.C. 154(b) by 461 days.

(21) Appl. No.: 12/907,613

(22) Filed: Oct. 19, 2010

(65) Prior Publication Data

US 2011/0090493 A1 Apr. 21, 2011

Related U.S. Application Data

(60) Provisional application No. 61/252,879, filed on Oct. 19, 2009.

(51) Int. Cl.
*H04N 7/18* (2006.01)
(52) U.S. Cl.
USPC .......................................................... 348/82
(58) Field of Classification Search
USPC .......................................................... 348/82
See application file for complete search history.

(56) References Cited

U.S. PATENT DOCUMENTS

| 4,699,463 | A | 10/1987 | D'Amelio et al. | |
|---|---|---|---|---|
| 4,980,763 | A | 12/1990 | Lia | |
| 5,682,199 | A * | 10/1997 | Lankford | 348/72 |
| 6,221,007 | B1 * | 4/2001 | Green | 600/160 |
| 2008/0026647 | A1 * | 1/2008 | Boehnlein et al. | 439/882 |
| 2009/0262354 | A1 * | 10/2009 | Horiuchi et al. | 356/445 |

* cited by examiner

*Primary Examiner* — David Czekaj
*Assistant Examiner* — Tracy Li
(74) *Attorney, Agent, or Firm* — Brinks Gilson & Lione

(57) ABSTRACT

A remote inspection device imager assembly includes an imager body having a male threaded portion. An accessory assembly includes: a tubular body portion having first internal female threads engaged with the male threaded portion such that tubular body portion rotation axially translates the tubular body portion with respect to the imager body; and a mirror obliquely angled with respect to a longitudinal axis of both the imager assembly. A threaded coupler positioned between the imager body and tubular body portion has second internal female threads engaged with the male threaded portion. The threaded coupler is selectively axially translated by rotation to a first contact position with the imager body or a second contact position with the tubular body portion. The second contact position binds the first and second internal female threads with the male threaded portion to prevent tubular body portion axial rotation and fix a mirror orientation.

17 Claims, 13 Drawing Sheets

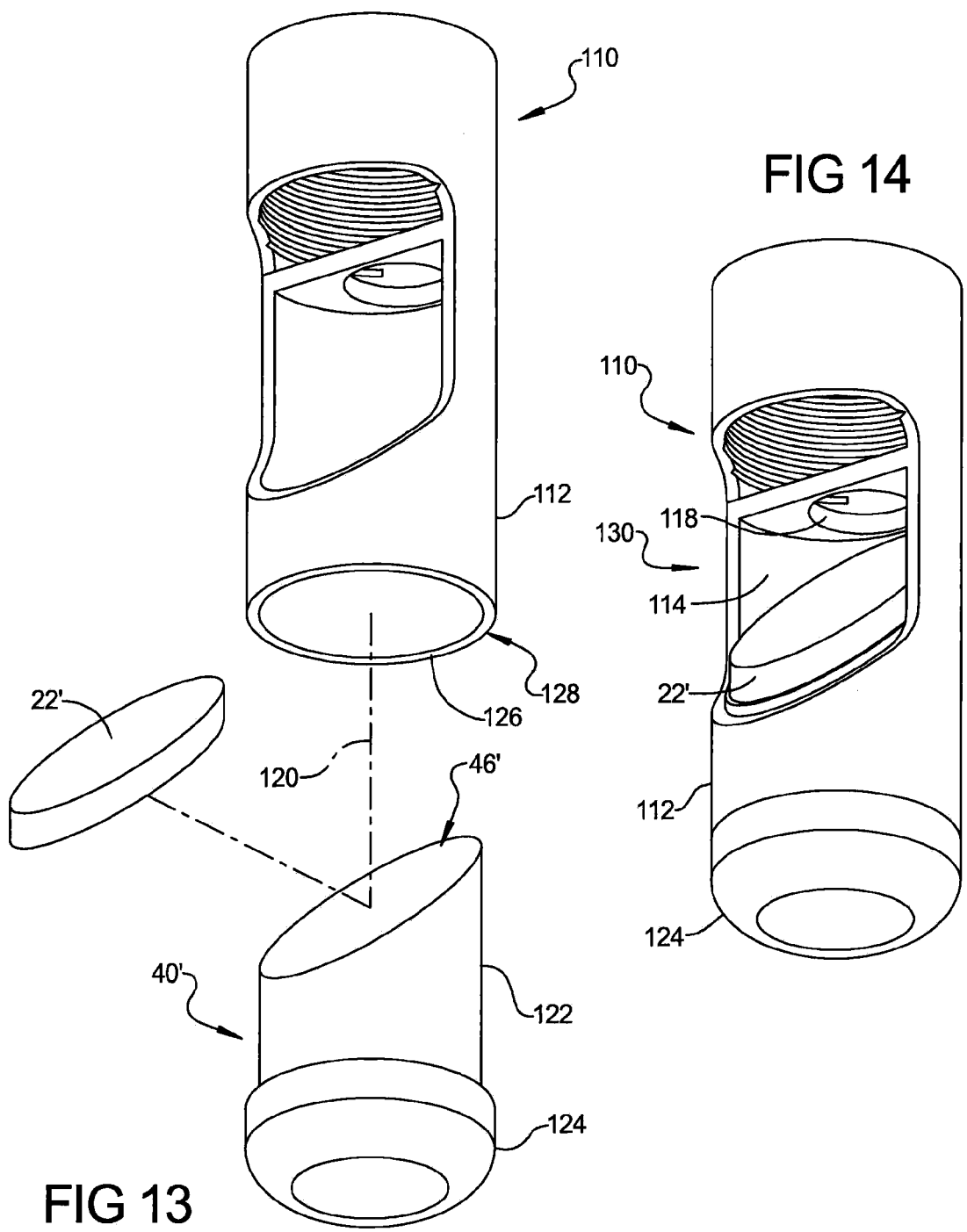

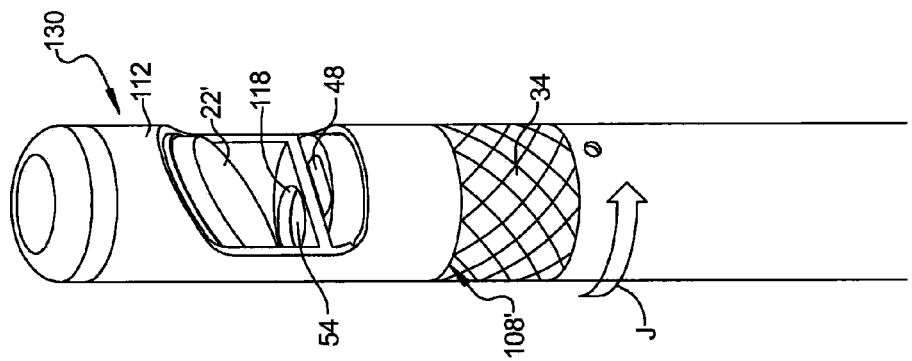
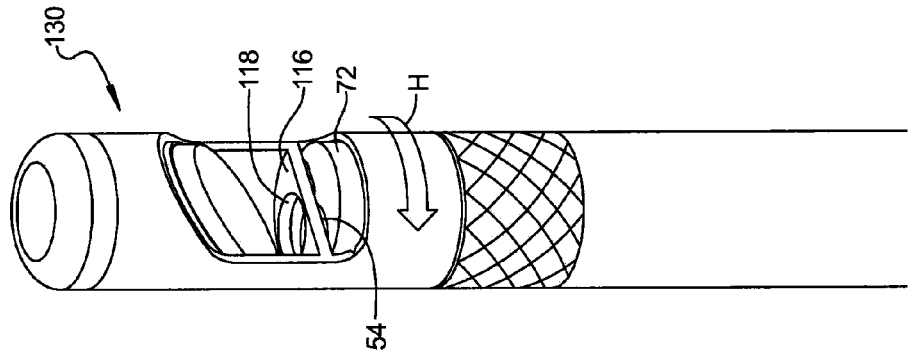
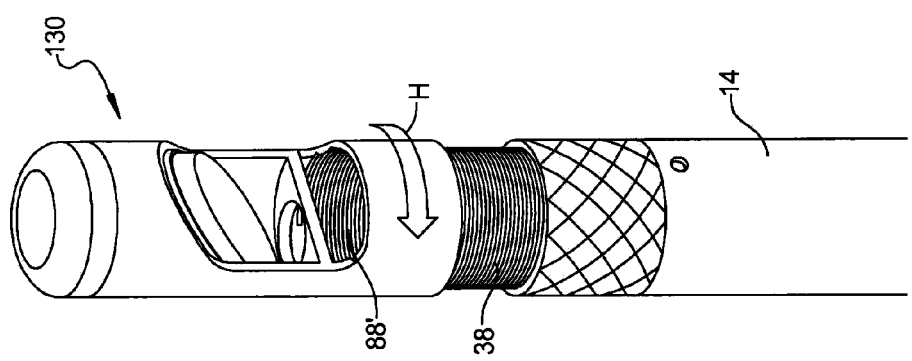
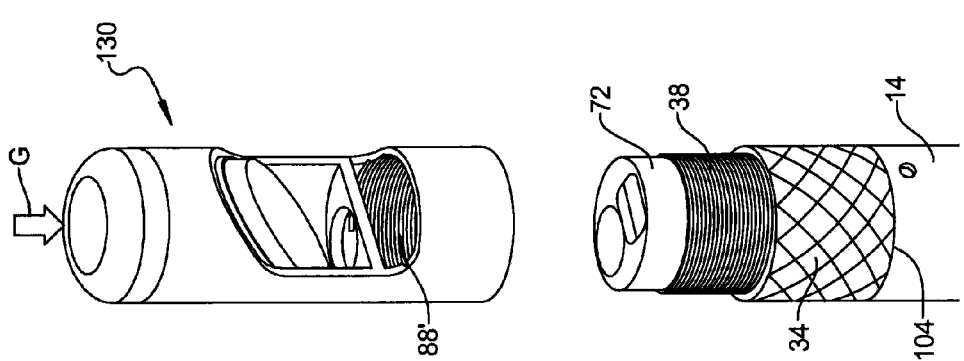

IMAGER HEAD ADJUSTABLE MIRROR MOUNT FOR BORESCOPE

CROSS-REFERENCE TO RELATED APPLICATION

This application claims the benefit of U.S. Provisional Application No. 61/252,879, filed on Oct. 19, 2009. The entire disclosure of the above application is incorporated herein by reference.

FIELD

The present disclosure relates borescopes and video scopes.

BACKGROUND

This section provides background information related to the present disclosure which is not necessarily prior art.

Borescopes and video scopes used for inspecting visually obscure locations, hereinafter referred to as remote inspection devices, are typically tailored for particular applications. For instance, some remote inspection devices have been tailored for use by plumbers to inspect pipes and drains. Likewise, other types of remote inspection devices have been tailored for use by mechanics to inspect interior compartments of machinery being repaired.

Remote inspection devices which include a mirror in a remote imager body are known which angularly orient the mirror to provide a viewing field with respect to a longitudinal axis of the imager body. Such mirror devices are used to reflect light from a light source outward toward an object to be viewed. The mirror is also used to redirect light reflected from the object into an image transmission device. When both the transmitted light and received image reflected light encounter the mirror, haloing often occurs which blocks or degrades a portion of the received image due to the transmitted light. Because a space envelope of the imager body is minimized to maximize the spaces it can be manipulated into, moving the transmitted light significantly away from the mirror space devoted to receiving the illuminated object image may not be possible.

SUMMARY

This section provides a general summary of the disclosure, and is not a comprehensive disclosure of its full scope or all of its features.

According to several embodiments of the present disclosure, an imager assembly for a remote inspection device includes an imager body having a male threaded portion. An accessory assembly includes: a tubular body portion having first internal female threads engaged with the male threaded portion of the imager body such that rotation of the tubular body portion axially translates the tubular body portion with respect to the imager body; and a mirror obliquely angled with respect to a longitudinal axis of both the imager body and the accessory assembly. A threaded coupler positioned between the imager body and the tubular body portion has second internal female threads engaged with the male threaded portion such that the threaded coupler is selectively axially translated by rotation to a first contact position with the imager body or a second contact position with the tubular body portion, the second contact position operating to bind the first and second internal female threads with the male threaded portion to prevent axial rotation of the tubular body portion and fix an orientation of the mirror.

According to other embodiments, the imager assembly further includes an imager device retained on a printed circuit board in the imager body. An imager window receives light reflected from an object. An LED emits light through a light pipe to illuminate the object. A proximate end of the mirror is positioned closest to the imager window and farthest from the light pipe.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 13 is a front left perspective assembly view of the tubular body portion of FIG. 9 prior to insertion of a mounting cap to create the accessory assembly;

FIG. 14 is a front left perspective view of the assembled accessory assembly of FIG. 13;

FIG. 15 is a front right perspective assembly view of the accessory assembly of FIG. 14 prior to installation on an imager body;

FIG. 16 is a front right perspective assembly view of the accessory assembly of FIG. 15 shown partially assembled;

FIG. 17 is a front right perspective assembly view of the accessory assembly of FIG. 16 in an aligned position;

FIG. 18 is a front right perspective assembly view of the accessory assembly of FIG. 17 in a locked position.

Corresponding reference numerals indicate corresponding parts throughout the several views of the drawings.

DETAILED DESCRIPTION

Figure 1:
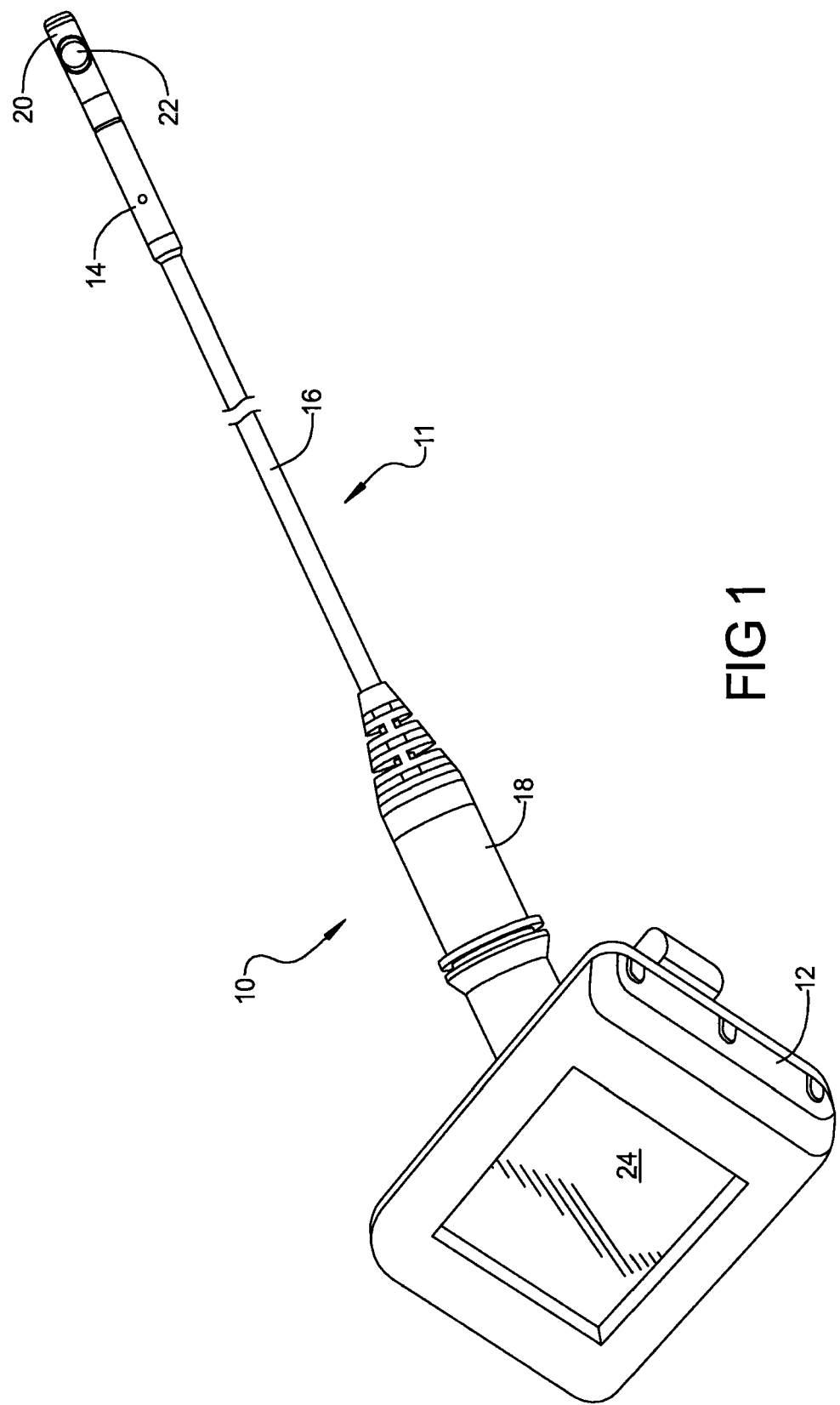
FIG. 1 is a front left perspective view of a remote inspection device assembly having an imager head adjustable mirror mount of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Referring to FIG. 1, a remote inspection device assembly 10 includes a flexible member/imager head assembly 11 connected to an image display unit 12. Image display unit 12 receives images converted to electronic signals from an imager body 14 of flexible member/imager head assembly 11 which is connected to image display unit 12 by a flexible member 16 of flexible member/imager head assembly 11. A connector body 18 of flexible member/imager head assembly 11 is releasably connected to image display unit 12 to directly couple flexible member 16 to image display unit 12. An accessory assembly 20 is releasably connected to imager body 14. A mirror 22 is mounted in the accessory assembly 20 to reflect light generated in imager body 14 outward to illuminate an object positioned proximate to accessory assembly 20 and to redirect reflected light from the object into imager body 14. The flexible member 16 allows imager body 14 together with accessory assembly 20 to be remotely manipulated to better receive light reflected from the object. Image display unit 12 provides a viewing screen 24 to display the object's image. A length of flexible member 16 can be varied between multiple embodiments.

Figure 2:
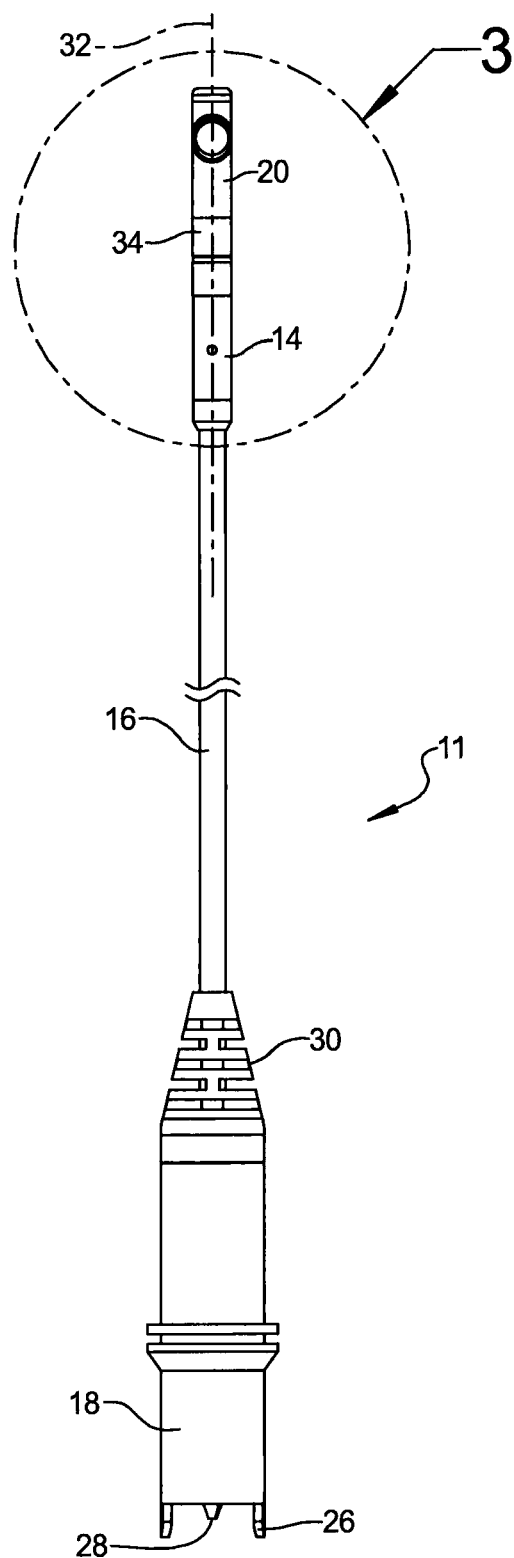
FIG. 2 is a front elevational view of a flexible member/imager head assembly of the remote inspection device of FIG. 1.

Referring to FIG. 2 and again to FIG. 1, connector body 18 can include one or more anti-rotation elements extending axially therefrom which engage with image display unit 12 to prevent axial rotation of connector body 18, flexible member 16, and imager body 14. At least one electrical contact pin 28 also extends from connector body to electrically couple imager body 14 to image display unit 12. A strain relief 30 positioned directly at the connection between flexible member 16 and connector body 18 reduces bending strain of the flexible member where it couples to connector body 18. As previously noted, imager body 14 is not axially rotatable with respect to a longitudinal axis 32 of imager body 14 and flexible member 16. Accessory assembly 20 is threadably connected to imager body 14 by axial rotation of accessory assembly 20 with respect to longitudinal axis 32. A threaded coupler 34 is rotated into engagement with accessory assembly 20 to releasably fix an axial and longitudinal position of accessory assembly 20 with respect to imager body 14.

Figure 3:
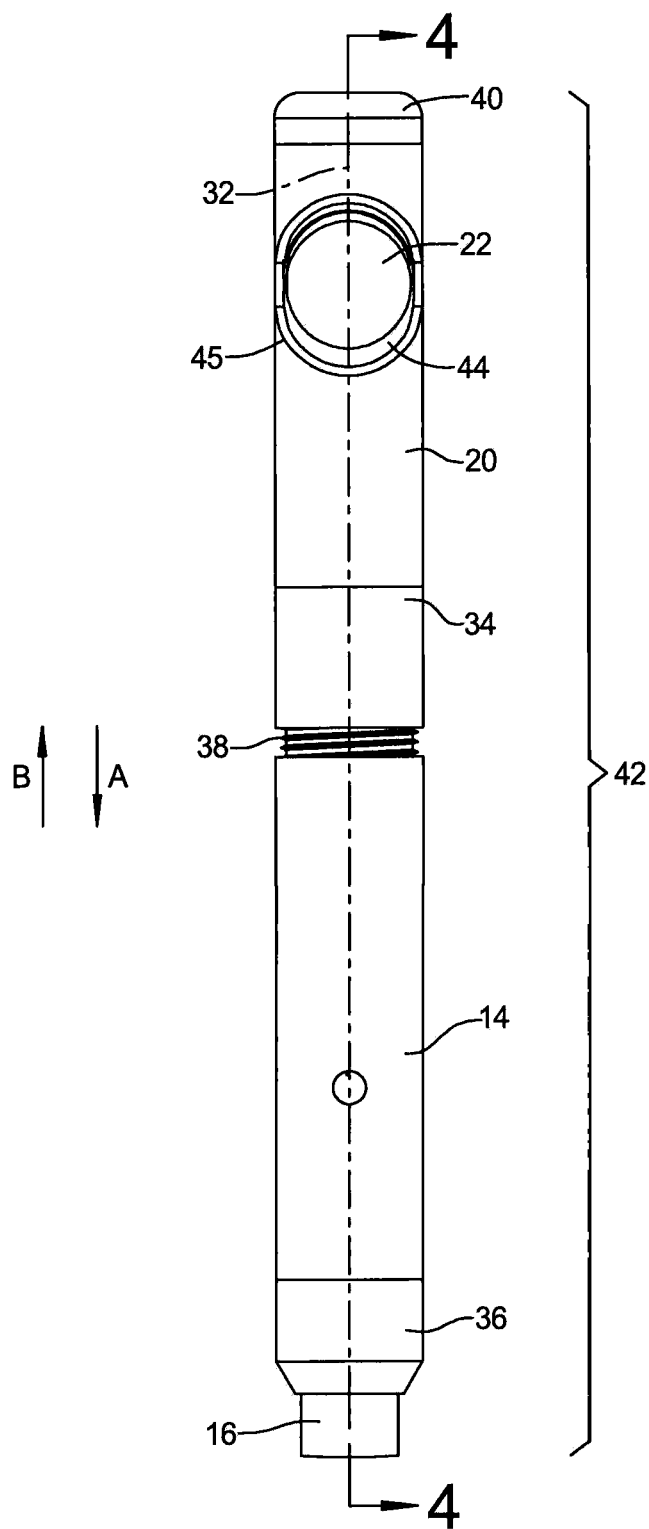
FIG. 3 is a front elevational view of area 3 of FIG. 2.

Referring to FIG. 3, a joining member 36 couples imager body 14 to flexible member 16. Both accessory assembly 20 and threaded coupler 34 have internal female threads (not shown in this view) which are threaded onto a male threaded portion 38 of threaded imager body 14. Accessory assembly 20 includes a mounting cap 40 to which mirror 22 is fixed. Mirror 22 is angularly oriented with respect to longitudinal axis 32. When coupled together, accessory assembly 20, threaded coupler 34, imager body 14, and joining member 36 together create an imager assembly 42. Mounting cap 40 and mirror 22 are connected to accessory assembly 20 such that mirror 22 is aligned with a light receiving cavity 44 created in a tubular body portion 45 of accessory assembly 20. Reflected light from an object is received through light receiving cavity 44 of tubular body portion 45 and redirected by mirror 22 (downwards as viewed in FIG. 3) into imager body 14. The threaded coupler 34 is positioned as shown in a locked position to axially and rotationally fix accessory assembly 20 together with mirror 22 to imager body 14. Threaded coupler 34 and accessory assembly 20 can individually be axially moved by threaded engagement with threaded portion 38 in either an insertion direction "A" or an opposite extension direction "B".

Figure 4:
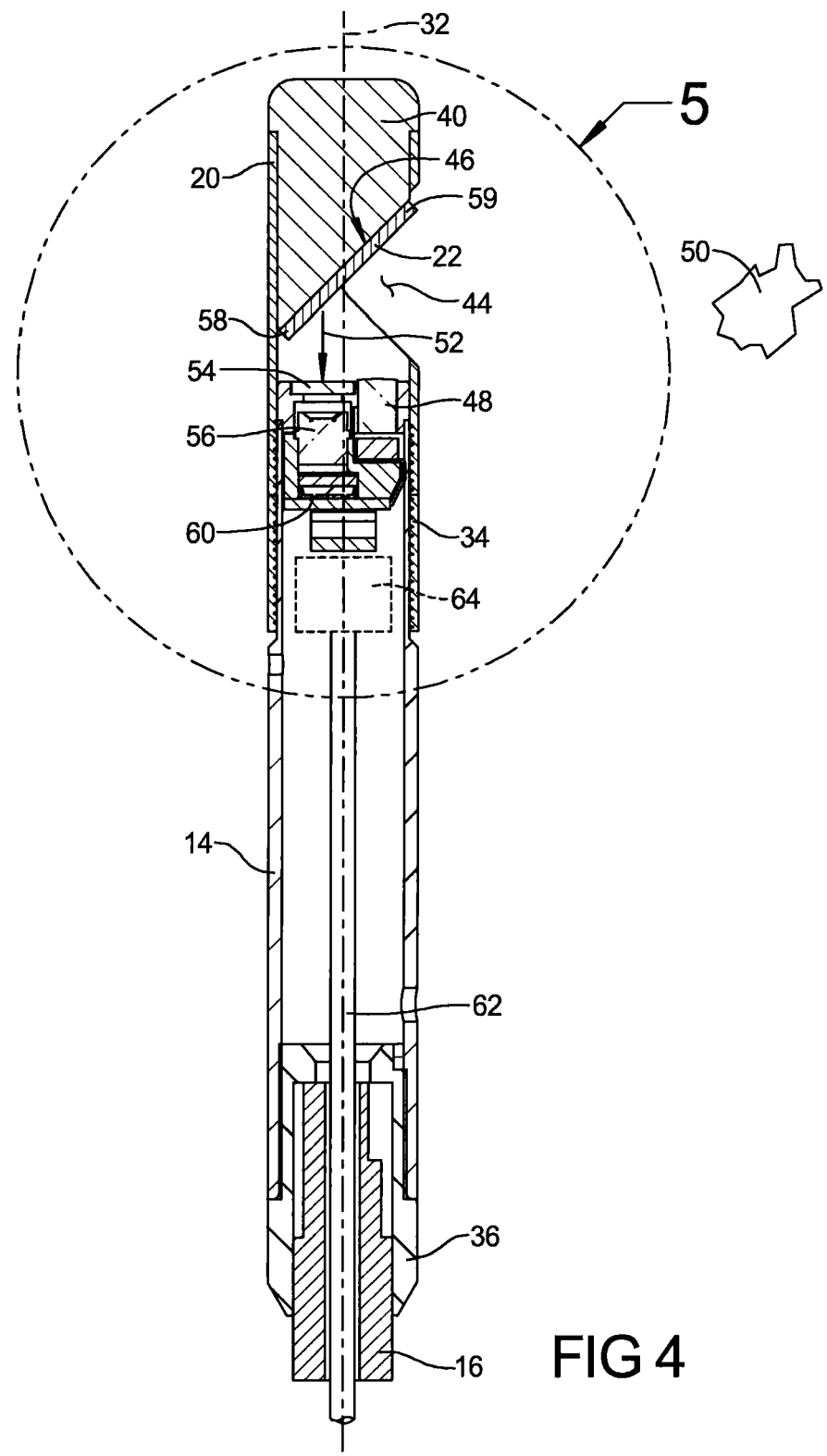
FIG. 4 is a cross sectional side elevational view taken at section 4 of FIG. 3.

Referring to FIG. 4, mirror 22 is obliquely angled with respect to longitudinal axis 32 and is fixed to a mirror mount pad 46 of mounting cap 40. Light generated in imager body 14 is transmitted outward from a light pipe 48 and reflected off mirror 22 through light receiving cavity 44 to illuminate an object 50. The illuminated image of object 50 as reflected light is received through light receiving cavity 44 and is redirected by mirror 22 along an exemplary light ray path 52 into an imager window 54 for subsequent transmission through a lens 56. A proximate end 58 of mirror 22 is positioned closest to imager window 54 and farthest from light pipe 48 to minimize haloing in the received reflected image of object 50 by light impinging on mirror 22 transmitted from light pipe 48. Conversely, an opposite or distal end 59 of mirror 22 is positioned farthest away (with respect to longitudinal axis 32) from imager window 54 and axially aligned with respect to light pipe 48. A printed circuit board 60 transmits electric signals representing the image of the object 50 to a wire set 62. A coiled wire zone 64 is provided to provide axial extension or retraction of wire set 62 due to bending of flexible member 16.

Referring to FIG. 5 and again to FIG. 4, according to several embodiments only a single high wattage light emitting diode (LED) 66 is provided to transmit light through light pipe 48. Lens 56 is supported by a lens holder 68 which is contoured to provide space for an imager device 70 such as a CMOS imager. Imager device 70 receives the light rays reflected back from object 50 and converts the light images to electric signals. Imager device 70 is electrically connected to printed circuit board 60. An imager cap 72 is then positioned proximate to lens 56 to support imager window 54 and light pipe 48 and to connect (by adhesive bonding or mechanical connection) to an inner wall 74 of tubular body portion 45. A counter-bore shoulder 76 of imager cap 72 axially abuts a free end of imager body 14 when imager cap 72 is mounted in insertion direction "A". Accessory assembly 20 is slidably received over a perimeter surface of imager cap 72 when accessory assembly 20 is threadably connected to male threaded portion 38 of imager body 14. A distance "C" separating proximate end 58 of mirror 22 from imager window 54 is minimized and a distance "D" separating distal end 59 of mirror 22 from imager window 54 is maximized to minimize haloing of the image received through imager window 54 by positioning the portion of mirror 22 (distal end 59) from which light from LED 66 is reflected farthest away from imager window 54. An obtuse or oblique angle α is created between longitudinal axis 32 and a reflective surface 77 of mirror 22 to permit viewing objects located transversely with respect to longitudinal axis 32.

Figure 6:
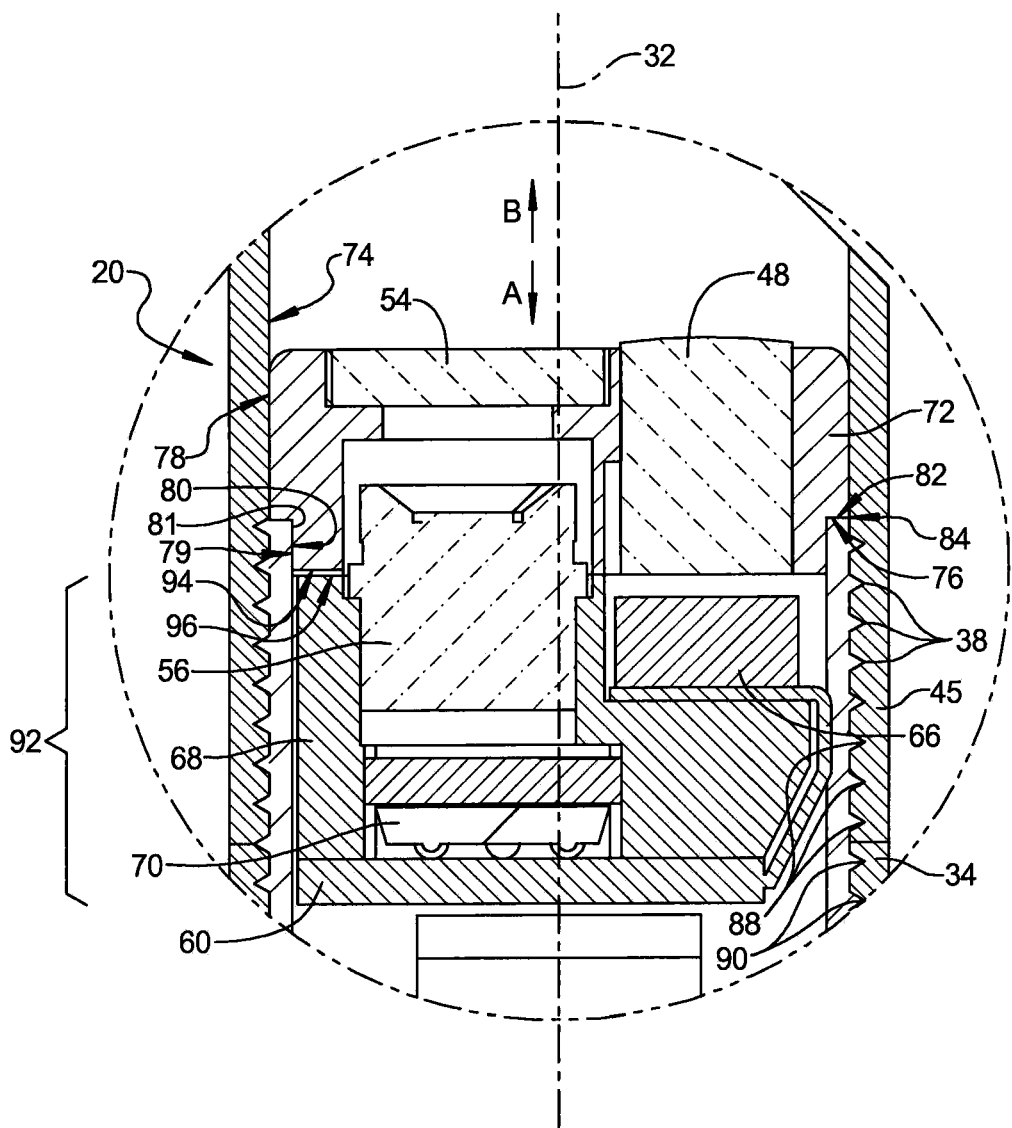
FIG. 6 is a cross sectional side elevational view of area 6 of FIG. 5.

Referring to FIG. 6, inner wall 74 of tubular body portion 45 is slidably received with respect to an outer surface 78 of imager cap 72. A circumferential wall 79 of imager cap 72 is fixedly connected to an inner wall 80 of imager body 14 for example using a water resistant adhesive 81. Accessory assembly 20 thereafter rotates and axially translates in either insertion direction "A" or the extension direction "B" with respect to both imager cap 72 and imager body 14. Accessory assembly 20 can be rotated with respect to longitudinal axis 32 to axially translate accessory assembly 20. Contact of an un-threaded portion of tubular body portion 45 and imager body 14 proximate the counter-bore shoulder 76 of imager cap 72 and a free end 82 of male threaded portion 38 of imager body 14 occurs at a positive stop point 84 of accessory assembly 20. When threaded onto imager body 14 accessory assembly 20 can be axially translated independently of threaded coupler 34 to provide the optimum position or spacing of lens 56 and imager window 54 with respect to mirror 22. Thereafter, when threaded coupler 34 contacts accessory assembly 20 opposite forces are created between first internal female threads 88 of tubular body portion 45 and second internal female threads 90 of threaded coupler 34 with respect to male threaded portion 38 of imager body 14 to bind a position of accessory assembly 20 with respect to imager body 14 axially and rotationally.

A component assembly 92 includes lens 56, printed circuit board 60, LED 66, lens holder 68, and imager device 70. Component assembly 92 is loaded into imager body 14 and positioned such that a surface 94 of imager cap 72 is proximate to or in direct contact with an opposed surface 96 of lens holder 68. According to several embodiments component assembly 92 can be fixed to imager body 14 for example by adhesive bonding.

Referring to FIG. 7 and again to FIG. 4, to minimize halo effects accessory assembly 20 is threadably connected to imager body 14 and rotated until proximate end 58 of mirror 22 is at its closest separation distance with respect to imager window 54. Because the positions of proximate end 58 and imager window 54 are not visible to the installer of accessory assembly 20, to visually help align mirror 22 in its predetermined position with respect to imager window 54, first and second markings 98, 100 are provided. First marking 98 is created on imager body 14 and second marking is created on tubular body portion 45 each parallel with longitudinal axis 32. A visible indication of the correct alignment of proximate end 58 of mirror 22 with imager window 54 is provided when first and second markings 98, 100 are co-axially aligned with each other. First and second markings 98, 100 are therefore co-axially aligned as shown prior to fixing the position of threaded coupler 34 in contact with tubular body portion 45. Markings 98, 100 can be laser etchings, or in other forms, for example indentations, painted or silk screened lines, and the like.

Figure 7:
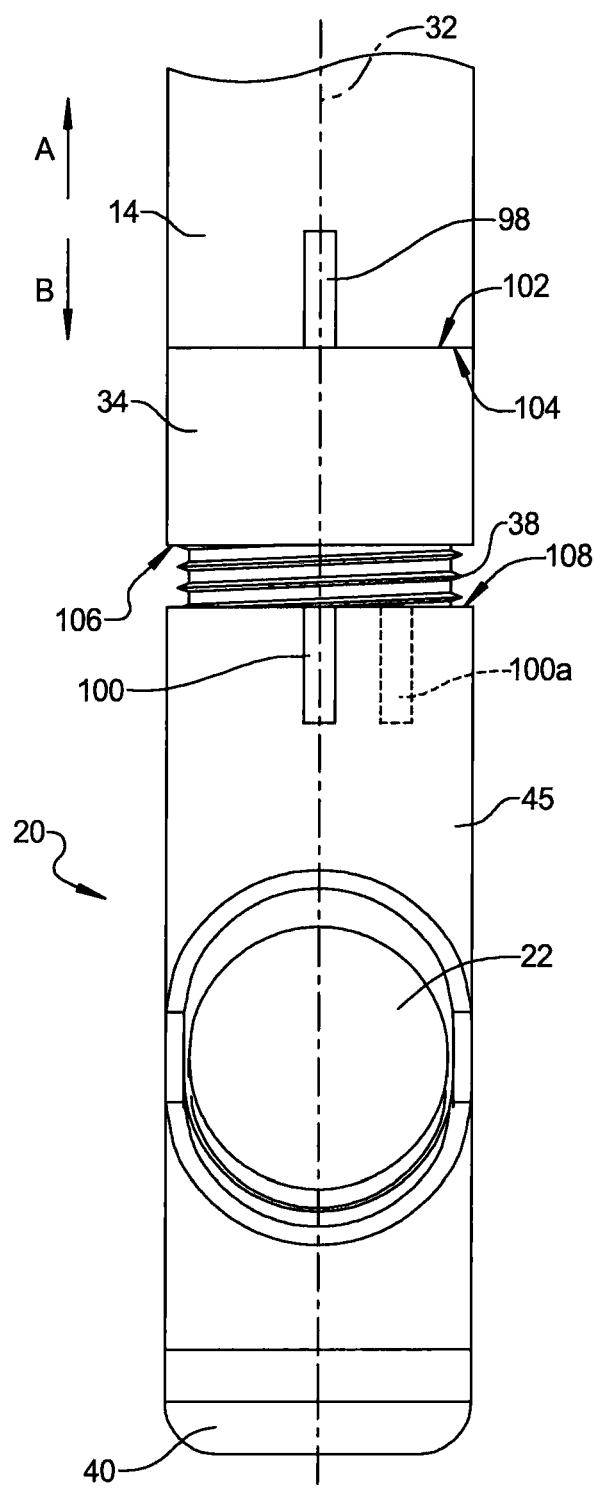
FIG. 7 is a front elevational view of an imager having an accessory assembly of FIG. 1.
Figure 8:
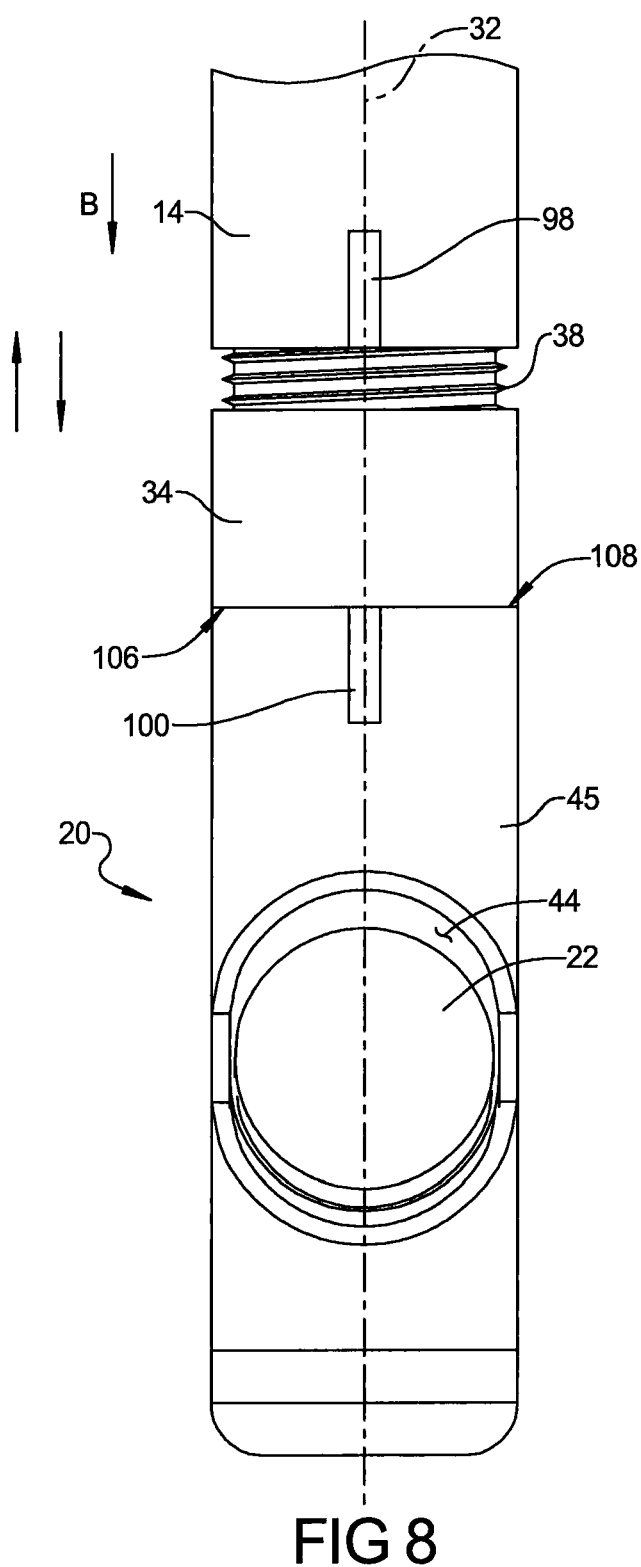
FIG. 8 is a front elevational view modified from FIG. 8 to show a fixed position of the accessory assembly.

Referring to FIGS. 6-8, adjustment and axial position fixing of mirror 22 is accomplished as follows using threaded coupler 34. First, as best seen in FIG. 7 threaded coupler 34 is threaded to translate it in insertion direction "A" all the way onto male threaded portion 38 of imager body 14 until a first coupler end 102 contacts an end face 104 of imager body 14. Second, accessory assembly 20 is threaded onto male threaded portion 38 until the positive stop point 84 described in reference to FIG. 6 is contacted. This may not provide co-axial alignment of first and second markings 98, 100 because second marking 100 may be in an over-rotated position 100a when positive stop point 84 is contacted. To then align first and second markings 98, 100, and referring next to FIG. 8, accessory assembly 20 is unscrewed (in a counter-clockwise direction if male threaded portion 38 includes right-handed threads, or vice versa) until first and second markings 98, 100 visually co-axially align with each other. Threaded coupler 34 is then rotated to move threaded coupler 34 in the extension direction "B" until a second coupler end 106 contacts a receiving face 108 of tubular body portion 45. Further application of torque to threaded coupler 34 oppositely binds the internal female threads of threaded coupler 34 and the internal female threads of tubular body portion 45 with the male threaded portion 38 to prevent further rotation of tubular body portion 45 with respect to imager body 14 which constrains tubular body portion 45 and therefore mirror 22 both axially and rotationally.

In additional embodiments, a male imager cap thread is created on outer surface 78 of imager cap 72 which can be threadably engaged with first internal female threads 88. In these embodiments, the threaded coupler 34 can be eliminated because the imager cap 72 will independently lock with respect to tubular body portion 45 when imager cap 72 is contacted by imager body 14. According to other embodiments, a set screw, a key/slot combination, or a similar device can be used in place of threaded coupler 34 to fix the position of mirror 22 with respect to lens 56.

Figure 9:
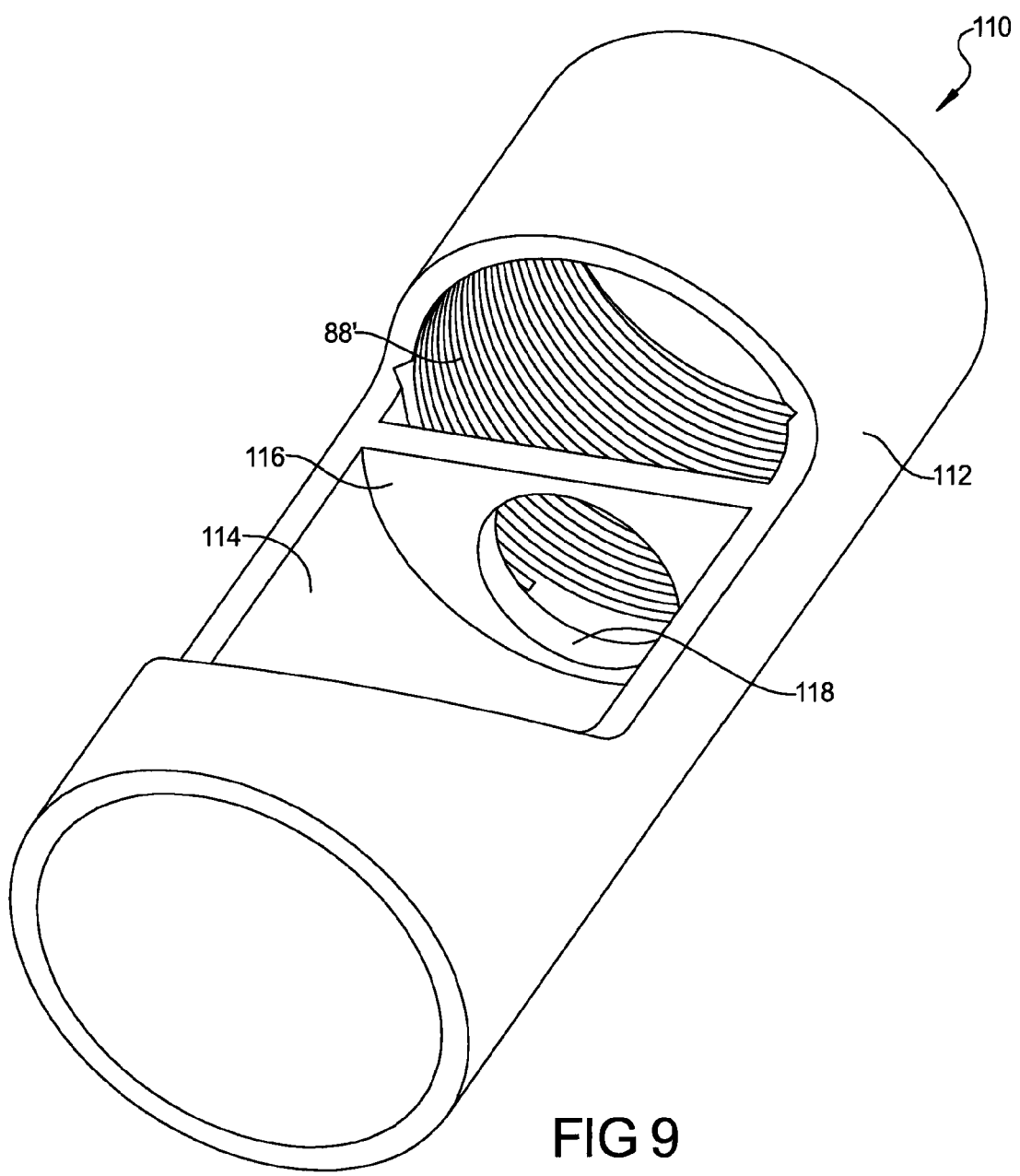
FIG. 9 is a top right perspective view of another embodiment for a tubular body portion of an accessory assembly.

Referring to FIG. 9 and again to FIGS. 4 and 6, a tubular body portion 110 for another embodiment of an accessory assembly is modified from tubular body portion 45. Tubular body portion 110 includes a tubular body 112 having a light receiving cavity 114 that is separated from first internal female threads 88' by a partial wall 116. Partial wall 116 can be oriented substantially perpendicular to the longitudinal axis 32. A light restricting aperture 118 having the form of a circular aperture is created in partial wall 116. Tubular body portion 110 is similarly threadably connected to male threaded portion 38 of threaded imager body 14 using first internal female threads 88' as shown in FIG. 6 for tubular body portion 45.

Figure 10:
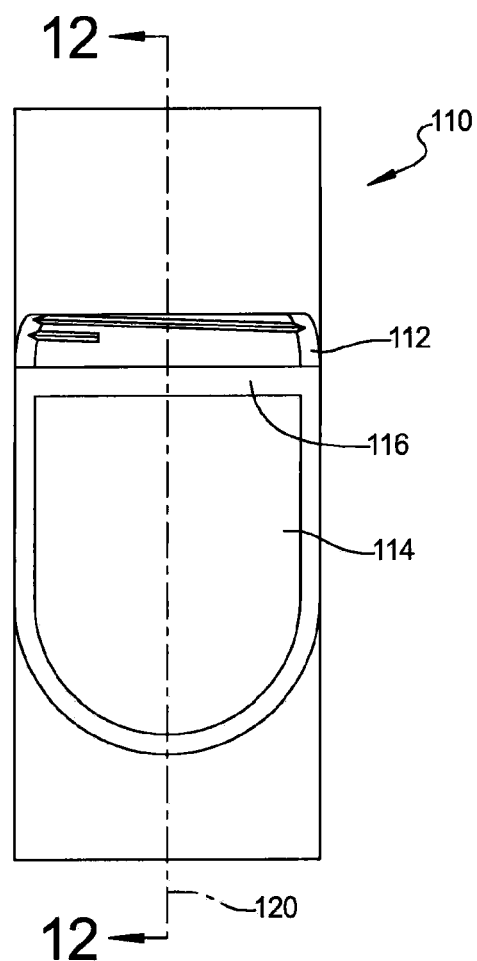
FIG. 10 is a front elevational view of the tubular body portion of FIG. 9.

Referring to FIG. 10, both light receiving cavity 114 and partial wall 116 are equally divided by a longitudinal axis 120 of tubular body portion 110. Partial body wall 116 can be a homogeneous portion of tubular body 112 or can be connected for example by welding to tubular body 112.

Figure 11:
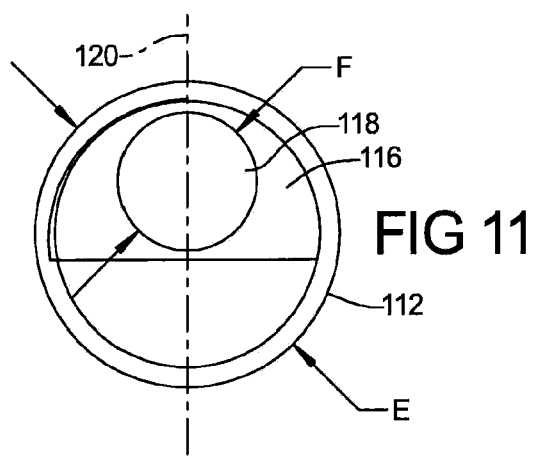
FIG. 11 is a top plan view of the tubular body portion of FIG. 9.
Figure 12:
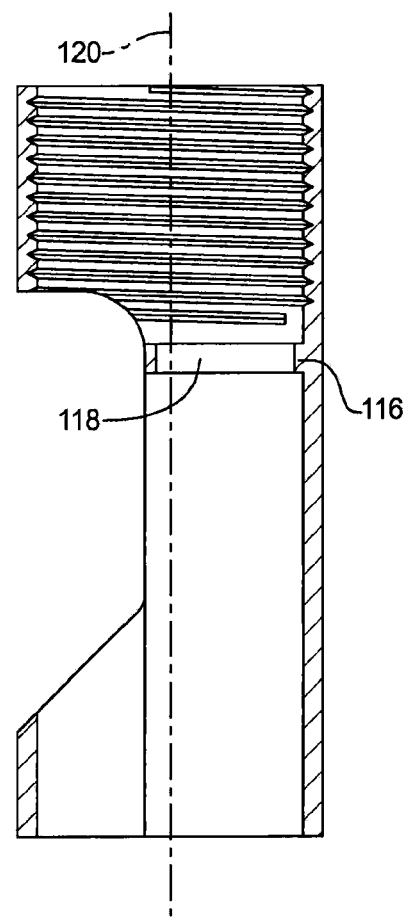
FIG. 12 is a cross sectional side elevational view taken at section 12 of FIG. 10.

Referring to FIGS. 11 and 12, a diameter "E" of tubular body 112 is larger than a diameter "F" of light restricting aperture 118. Light restricting aperture 118 is aligned on longitudinal axis 120 but is located off-center or away from the longitudinal center of tubular body 112.

Figure 5:
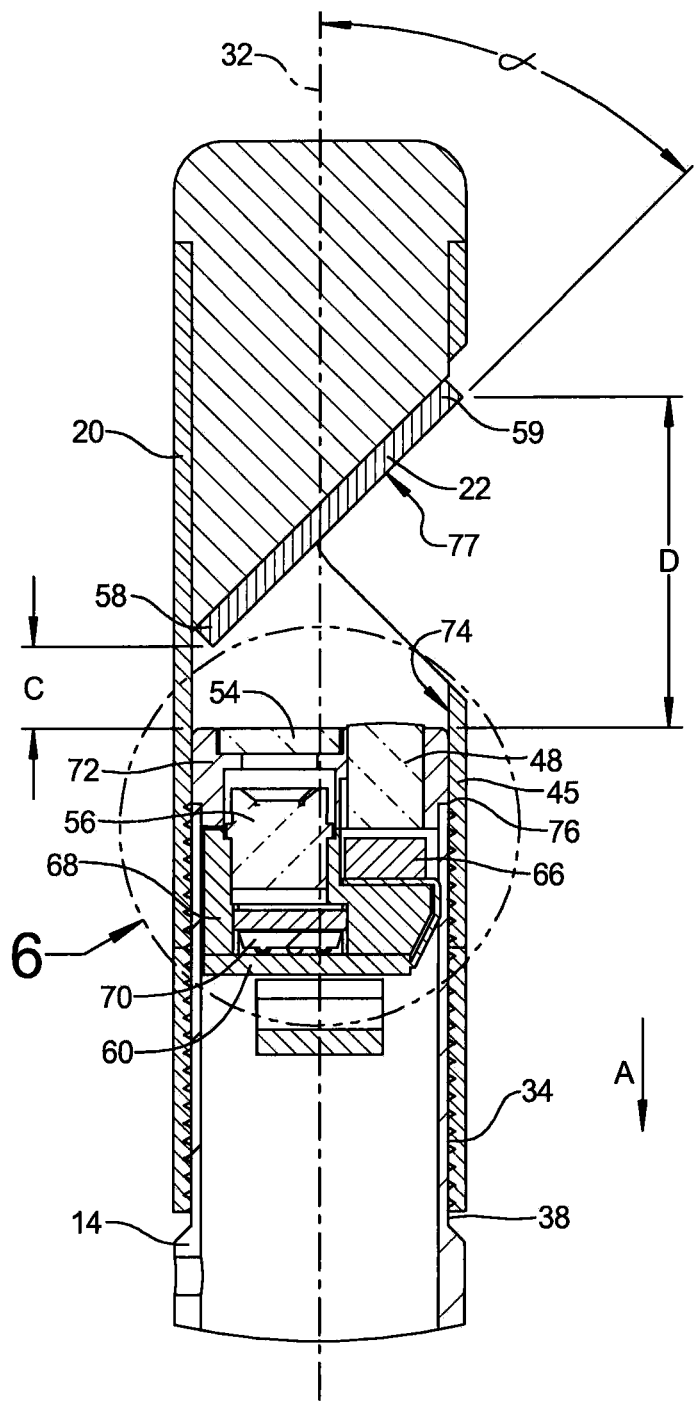
FIG. 5 is a cross sectional side elevational view of area 5 of FIG. 4.

Referring to FIG. 13 and again to FIGS. 4 and 5, mounting cap 40' includes a cylindrical body portion 122 and a larger diameter cap portion 124. Mirror 22' is fixed to mirror mount pad 46' before cylindrical body portion 122 is slidably received in a bore 126 of tubular body 112. Cap portion 124 contacts an end face 128 of tubular body 112 to act as a stop to prevent further sliding motion of cylindrical body portion 122 into bore 126.

Referring to FIG. 14, an accessory assembly 130 is formed when cap portion 124 of mounting cap 40' contacts tubular body 112 and mirror 22' is aligned in light receiving cavity 114 to direct light received in light receiving cavity 114 through light restricting aperture 118.

Referring to FIGS. 15-18 the installation sequence of accessory assembly 130 is as follows. Threaded coupler 34 is initially positioned in contact with end face 104 of imager body 14. Accessory assembly 130 is moved in a longitudinal installation direction "G" to align first internal female threads 88' to slide over imager cap 72. As shown in FIG. 16, when first internal female threads 88' contact male threaded portion 38, accessory assembly 130 is rotated in a clockwise direction of rotation "H" to threadably engage accessory assembly 130 with imager body 14. As shown in FIG. 17, accessory assembly 130 is continually rotated in the clockwise direction "H" until partial wall 116 approaches imager cap 72. Accessory assembly 130 is then further rotated to align light restricting aperture 118 with imager window 54. As shown in FIG. 18, with light restricting aperture 118 aligned with imager window 54, threaded coupler 34 is rotated in a counterclockwise direction of rotation "J" until threaded coupler 34 contacts receiving face 108' of tubular body 112, releasably binding threaded coupler 34 on male threaded portion 38 to lock accessory assembly 130 against rotation in any direction with respect to imager body 14. To subsequently release and/or further adjust accessory assembly 130, tubular body 112 is held while rotating threaded coupler 34 in the clockwise direction of rotation "H".

Figure 19:
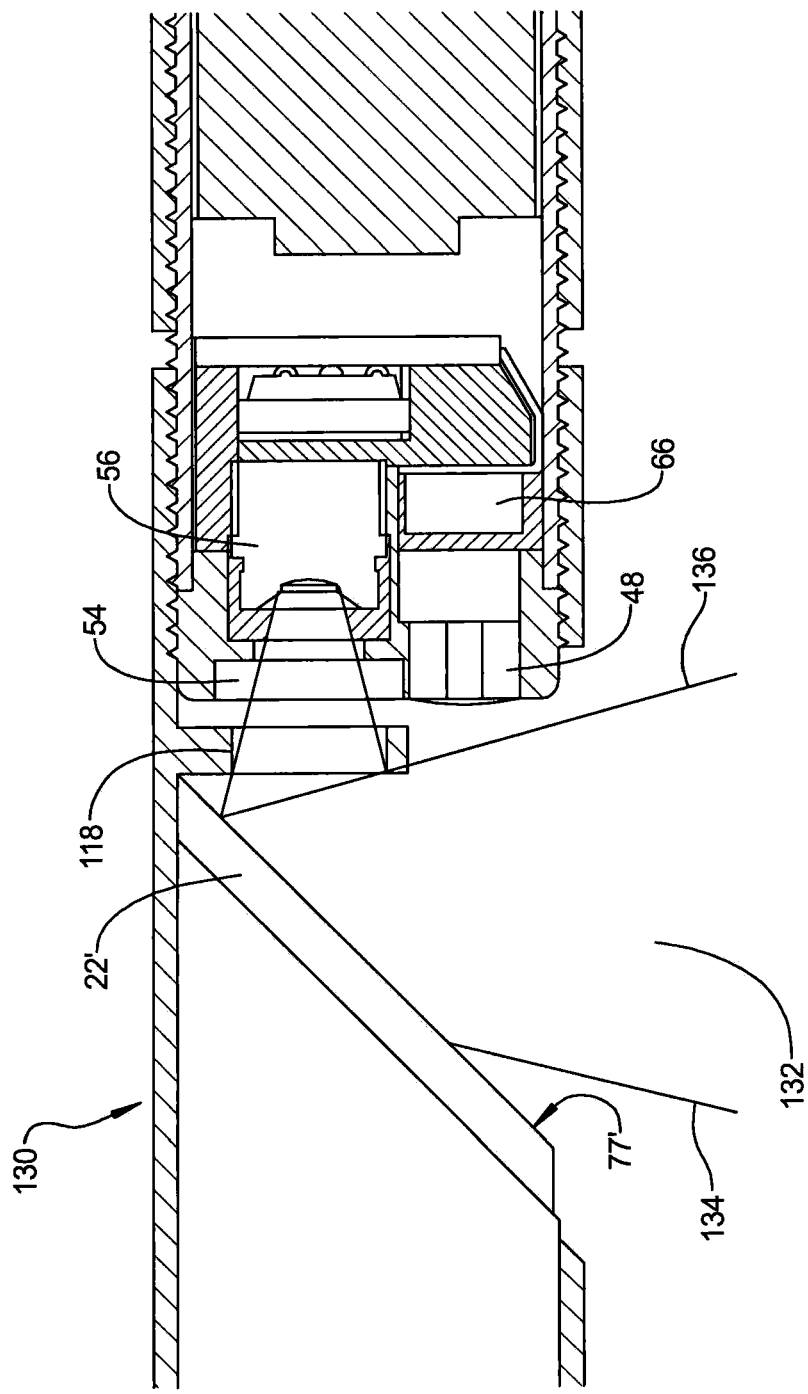
FIG. 19 is a partial cross sectional side elevational view of the accessory assembly of FIG. 18.

Referring to FIG. 19 and again to FIG. 11, the diameter "F" of light restricting aperture 118 is selected to prevent light generated by LED 66 and emitted through light pipe 48 from being reflected off reflective surface 77' of mirror 22' into imager window 54 and therefore into lens 56. A window 132 of a plurality of possible light rays that can be reflected into lens 56 through light restricting aperture 118 is bounded by first and second window borders 134, 136. As apparent from the position of second window border 136 which does not contact light pipe 48, any path of light rays emitted at any angle from light pipe 48 cannot be directly reflected off reflective surface 77' to reach lens 56.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An imager assembly for a remote inspection device, comprising:
    an imager body having a male threaded portion; an accessory assembly, including:
        a tubular body portion having first internal female threads engaged with the male threaded portion of the imager body such that rotation of the tubular body portion axially translates the tubular body portion with respect to the imager body; and
        a mirror obliquely angled with respect to a longitudinal axis of the accessory assembly; and
        a threaded coupler positioned between the imager body and the tubular body portion having second internal female threads engaged with the male threaded portion such that the threaded coupler is selectively axially translated by rotation to a contact position where the threaded coupler contacts the tubular body portion, the contact position operating to bind the first and second internal female threads with the male threaded portion to prevent axial rotation of the tubular body portion and fix an orientation of the mirror.

2. The imager assembly of claim 1, further comprising:
    a light receiving cavity created in the tubular body portion of the accessory assembly for receiving light reflected from an object; and a mounting cap connected to the tubular body portion having a mirror mount pad, the mirror being fixed to the mirror mount pad at an oblique angle with respect to the longitudinal axis.

3. The imager assembly of claim 2, wherein the accessory assembly further includes an LED aligned with and operating to emit light through a light pipe, the light pipe aligned to reflect the light off the mirror and out of the tubular body portion through the light receiving cavity and toward the object.

4. The imager assembly of claim 3, wherein the accessory assembly further includes an imager window positioned proximate to the light pipe, the imager window operating to receive light reflected off the object and the mirror through the light receiving cavity into a lens.

5. The imager assembly of claim 4, wherein the tubular body portion is rotated until a proximate end of the mirror is positioned closest to the imager window and furthest from the light pipe.

6. The imager assembly of claim 2, further including:
    a first marking created on the imager body; and a second marking created on the tubular body portion, the second marking when co-axially aligned with the first marking visually indicating alignment of a reflective surface of the mirror with the light receiving cavity.

7. The imager assembly of claim 6, wherein the threaded coupler is positioned in the contact position after co-axially aligning the first and second markings to fix the mirror alignment with the light receiving cavity.

8. The imager assembly of claim 4, wherein the tubular body portion further includes a partial wall oriented substantially perpendicular to the longitudinal axis.

9. The imager assembly of claim 8, further including a light restricting aperture created through the partial wall sized to prevent light emitted by the light pipe from directly reflecting off the mirror and through the imager window to reach the lens.

10. An imager assembly for a remote inspection device, comprising:
an imager body having a male threaded portion; an accessory assembly, including:
a tubular body portion having first internal female threads engaged with the male threaded portion of the imager body such that rotation of the tubular body portion axially translates the tubular body portion with respect to the imager body, the tubular body portion further comprising an aperture; and
a mirror obliquely angled with respect to the longitudinal axis of the accessory assembly; and
a threaded coupler positioned between the imager body and the tubular body portion, the threaded coupler having second internal female threads engaged with the male threaded portion such that the threaded coupler is selectively axially translated to a contact position with the tubular body portion, wherein the first and second internal female threads bind with the male threaded portion to prevent axial rotation of the tubular body portion and fix an orientation of the aperture.

11. The imager assembly according to claim 10, wherein the imager body further comprises an imager window at a free end of the imager body.

12. The imager assembly according to claim 11, wherein the contact position of the tubular body portion and the threaded coupler is configured to selectively align the aperture with the imager window.

13. A method for aligning an oblique mirror of an imager assembly for a remote inspection device, comprising:
rotationally connecting a threaded coupler to an imager body;
rotationally connecting a tubular body portion of an accessory assembly to the imager body, the accessory assembly comprising an aperture, the aperture being aligned parallel to the longitudinal axis of the imager body;
rotationally binding the threaded coupler and the tubular body portion such that the aperture is rotationally aligned with an imaging window of the imager body.

14. The method according to claim 13, wherein the accessory assembly comprises a mirror, the mirror being obliquely aligned with the longitudinal axis of the imager body.

15. The method according to claim 13, wherein the rotationally binding of the threaded coupler and the tubular body is configured to provide for a longitudinal space between the threaded coupler and an end face of the imager body.

16. The method according to claim 13, wherein the imager body comprises a male threaded portion.

17. The method according to claim 16, wherein the threaded coupler comprises first female internal threads, the tubular body comprises second female internal threads, and the binding occurs between the first female internal threads, the second female internal threads, and the male threaded portion.

* * * * *